(12) United States Patent
Van Beest

(10) Patent No.: US 9,060,880 B2
(45) Date of Patent: Jun. 23, 2015

(54) METHOD AND DEVICE FOR SLEEP POSTURE CORRECTION

(76) Inventor: Eline Christiane Van Beest, The Hague (NL)

( * ) Notice: Subject to any disclaimer, the term of this patent is extended or adjusted under 35 U.S.C. 154(b) by 151 days.

(21) Appl. No.: 13/695,209

(22) PCT Filed: May 4, 2010

(86) PCT No.: PCT/NL2010/000073
§ 371 (c)(1), (2), (4) Date: Oct. 29, 2012

(87) PCT Pub. No.: WO2011/139141
PCT Pub. Date: Nov. 10, 2011

(65) Prior Publication Data
US 2013/0043999 A1 Feb. 21, 2013

(51) Int. Cl.
| G08B 23/00 | (2006.01) |
| A61F 5/56 | (2006.01) |
| A61B 5/00 | (2006.01) |
| G08B 21/06 | (2006.01) |

(52) U.S. Cl.
CPC .............. *A61F 5/56* (2013.01); *A61B 5/4561* (2013.01); *G08B 21/06* (2013.01)

(58) Field of Classification Search
CPC ...... A61B 5/4561; A61B 5/6831; A61F 5/56; G08B 21/06; G08B 23/00
USPC ........... 340/573.7, 573.3, 575, 309.16, 309.7; 128/845, 848, 871; 600/301, 324, 333, 600/300
See application file for complete search history.

(56) References Cited

U.S. PATENT DOCUMENTS

| 4,617,525 | A | | 10/1986 | Lloyd |
| 5,038,137 | A | | 8/1991 | Lloyd |
| 5,081,447 | A | | 1/1992 | Echols |
| 5,381,801 | A | | 1/1995 | McShane et al. |
| 5,458,105 | A | * | 10/1995 | Taylor et al. .................. 128/848 |
| 5,914,660 | A | | 6/1999 | Mesibov et al. |
| 6,057,767 | A | | 5/2000 | Barnoach |
| 6,129,686 | A | * | 10/2000 | Friedman ....................... 600/595 |
| 6,356,203 | B1 | * | 3/2002 | Halleck et al. ................ 340/689 |
| 6,753,783 | B2 | * | 6/2004 | Friedman et al. ........... 340/573.7 |

(Continued)

FOREIGN PATENT DOCUMENTS

| CN | 101340869 | 1/2009 |
| EP | 2 407 131 A1 | 1/2012 |

(Continued)

OTHER PUBLICATIONS

Terry Young, Ph.D., et al; "The Occurence of Sleep-Disordered Breathing Among Middle-Aged Adults", The New England Journal of Medicine, vol. 328, No. 17, Apr. 23, 1993, pp. 1230-1235.

(Continued)

*Primary Examiner* — Hung T Nguyen
(74) *Attorney, Agent, or Firm* — Flener IP Law; Zareefa B. Flener

(57) ABSTRACT

In a sleep posture alerting method or an apparatus therefor, the sleep posture of a person is detected and the person is automatically alerted by an alerting device when the sleep posture is out of a predetermined body posture range. The detection of the sleep posture or at least the alerting of the person, when his/her body posture is out of the predefined body posture range, is deactivated during a sleep-in time period.

24 Claims, 4 Drawing Sheets

(56) References Cited

U.S. PATENT DOCUMENTS

| | | | |
|---|---|---|---|
| 6,765,489 B1 * | 7/2004 | Ketelhohn | 340/573.1 |
| 8,051,010 B2 | 11/2011 | Camenisch et al. | |
| 2008/0264426 A1 | 10/2008 | Walker | |
| 2008/0308112 A1 | 12/2008 | Aarts | |
| 2010/0087701 A1 | 4/2010 | Berka et al. | |
| 2011/0132378 A1 | 6/2011 | Levendowski et al. | |

FOREIGN PATENT DOCUMENTS

| | | |
|---|---|---|
| ES | 1070396 | 8/2009 |
| JP | 4-500325 | 1/1992 |
| JP | 2005-185650 | 7/2005 |
| JP | 2005-312901 | 10/2005 |
| JP | 2007-199025 | 8/2007 |
| JP | 2007-294143 | 8/2007 |
| JP | 05159173 | 12/2007 |
| WO | 2010/141893 A2 | 12/2010 |

OTHER PUBLICATIONS

Arie, Oksenberg, et al; "Association of Body Position With Severity of Apneic Events in Patients With Severe Nonpositional Obstructive Sleep Apnea", Chest Journal Official Publication of the American College of Chest Physicians, Oct. 2000; vol. 118, No. 4, pp. 1018-1024.

Wietske Richard, et al; "The Role of Sleep Position in Obstructive Sleep Apnea Syndrome", Eur Arch Otorhinolaryngol; vol. 263, pp. 946-950; Published Online: Jun. 27, 2006.

James J Bignold, B.Sc(BioS), et al; "Poor Long-Term Patient Compliance with the Tennis Ball Technique for Treating Positional Obstructive Sleep Apnea", Journal of Clinical Sleep Medicine, vol. 5, No. 5; Accepted for publication Jun. 2009; pp. 428-430.

Irene Permut, M.D., et al; "Comparision of Positional Therapy to CPAP in Patients with Positional Obstructive Sleep Apnea", Journal of Clinical Sleep Medicine, vol. 6, No. 3, Jun. 15, 2010; pp. 238-243.

M. Berger, et al; "Avoiding the supine position during sleep lowers 24 h blood pressure in obstructive sleep apnea (OSA) patients", Journal of Human Hypertension; Oct. 1997, vol. 11, No. 10, pp. 657-664.

Arie Oksenberg, PhD, et al; "Positional Therapy for Obstructive Sleep.Apnea Patients: A 6-Month Follow-Up Study", The Laryngoscope, vol. 116, Nov. 2006, pp. 1995-2000.

Arie Oksenberg, et al; "Positional vs Nonpositional Obstructive Sleep Apnea Patients: Anthropomorphic, Nocturnal Polysomnographic, and Multiple Sleep Latency Test Data", Chest Official Publication of the American College of Chest Physicians, Sep. 1997; vol. 112 No. 3, pp. 629-639.

Andrew S.L. Chan, et al; "Non-Positive Airway Pressure Modalities Mandibular Advancement Devices/Positional Therapy", Published in Proceedings of the American Thoracic Society, Feb. 15, 2008; vol. 5, No. 2, pp. 179-184.

Yoshiaki Itasaka, PhD, et al; "The Influence of Sleep Position and Obesity on Sleep Apnea", Published in Psychiatry and Clinical Neurosciences, Jun. 2000, vol. 54, Issue 3, pp. 255-384.

Rosalind Cartwright, et al; "A Comparative Study of Treatments for Positional Sleep Apnea", Published in Sleep, Dec. 1991, vol. 14, Issue 6, pp. 546-552.

Rosalind Cartwright, et al; "Sleep Position Training as Treatment for Sleep Apnea Syndrome: A Preliminary Study", vol. 8, Issue 2, Accepted for Publication Feb. 1985.

Kazuya Yoshida, DDS, PhD; "Influence of Sleep Posture on Response to Oral Appliance Therapy for Sleep Apnea Syndrome", Published in Sleep, vol. 24, No. 5, pp. 538-544, Accepted for Publication May 2001.

Jennifer H. Walsh, PhD, MSc, et al., "Influence of Head Extension, Flexion, and Rotation on Collapsibility of the Passive Upper Airway", Published in Sleep, vol. 31 No. 10, Accepted for Publication Jun. 2008, pp. 1440-1447.

Rémy C. Martin-Du Pan, et al; "The Role of Body Position and Gravity in the Symptoms and Treatment of Various Medical Diseases", Swiss Med Weekly, Sep. 18, 2004, vol. 134(37-38); pp. 543-551.

International Search Report: mailed Dec. 4, 2011; Appln. No. PCT/NL2010/000073.

* cited by examiner

METHOD AND DEVICE FOR SLEEP POSTURE CORRECTION

BACKGROUND OF THE INVENTION

The present invention relates to a method and a device for sleep posture correction.

In particular the present invention relates to a sleep posture alerting method, wherein the sleep posture of a person is detected and wherein the person is automatically alerted by an alerting device when the sleep posture is out of a predetermined body posture range.

The invention also relates to a sleep posture alerting apparatus, preferably to be worn on a body of a person, comprising
  an electronic control unit,
  a sensor operatively connected to the control unit for detecting the posture of the body, and
  an alarming device operatively connected to the control unit,
wherein, the sleep posture alerting device has a normal operational mode, in which—when the posture of the body detected by the sensor exits a predefined posture range—the control unit sends an alarm signal to the alarm device, and the alarming device generates an alarm based on the signal received from the control unit, to alert said person.

In U.S. Pat. No. 6,057,767 a sleep posture alerting apparatus of this type is disclosed. The known device having a gravity actuated sensor, a delay time circuit and a vibrator, which are placed within a housing. When the gravity activated sensor senses it is within a predetermined range of deviation from the horizontal, the device activates a vibrator. The vibrator irritates the device user, causing him to change his sleep posture, without waking him up.

The known sleep posture alert device measures posture and provides direct feedback when a person turns into certain positions. Considering the fact that the goal of the device is to avoid users from sleeping in certain positions, this method described could be seen as effective. However, the comfort level of the known device and method is of such poorness, that only a small percentage of the users is actually able to use the technique to help remain in certain positions. The result is great ineffectiveness of the desired effect: avoiding certain postures during the night.

The present invention has for an object to provide a method and apparatus for sleep posture correction which has an increased effectiveness.

SUMMARY OF THE INVENTION

According to one aspect of the invention this object is achieved by a sleep posture alerting apparatus, comprising
  an electronic control unit,
  a body posture detecting sensor operatively connected to the control unit for detecting the posture of the body, and
  an alarming device operatively connected to the control unit,
wherein, the sleep posture alerting device has a normal operational mode, in which—when the posture of the body detected by the sensor exits a predefined posture range—the control unit sends an alarm signal to the alarm device, and the alarming device generates an alarm based on the signal received from the control unit, to alert said person, wherein the control unit is programmed to switch the sleep posture device in said normal operational mode after an initial sleep-in time period.

According to the same aspect of the invention the object is achieved by a sleep posture alerting method, wherein the sleep posture of a person is detected and wherein the person is automatically alerted by an alerting device when the sleep posture is out of a predetermined body posture range, wherein the detection of the sleep posture or at least the alerting of the person, when his/her body posture is out of the predefined body posture range, is deactivated during a sleep-in time period.

To provide the most optimal night rest for users, sleeping with the proposed invention should optimally resemble a normal night of sleep, taking all relevant factors into account, for example the sleeping process, rhythm and postures. Therefore it is beneficial that the ability is provided to fall asleep in the naturally preferred position, even when this is the undesired posture to be corrected by the proposed invention during the night. This way, users of the proposed invention can fall asleep as they are used to, increasing the comfort level, and creating the most optimal environment for the natural sleep. Due to the maintenance of the comfort level when falling asleep, the threshold for a user to keep using the proposed invention is lowered and it will be easier for a user to continue using the proposed invention. Continued use enhances the learning process of sleeping in a new posture and that way the final solution effectiveness is increased. To enable this comfort and effectiveness level through providing the opportunity to fall asleep in a preferred posture, the proposed invention could use a period in which one can fall asleep whilst feedback by the proposed invention is excluded.

Preferably, the state of sleep of the person is detected and—when it is detected that the person is in a state of sleep—the detection of the sleep posture or the alerting of the person is activated such that, in the event that his/her body posture changes to a position out of the predefined body posture range, the person will be alerted.

Alternatively, the state of sleep of the person is assumed after a predetermined period of time, after which the detection of the sleep posture or the alerting of the person is activated such that, in the event that his/her body posture changes to a position out of the predefined body posture range, the person will be alerted. The mentioned predetermined period of time may be between 5 and 60 minutes, preferably between 10 and 30 minutes.

In a further alternative the state of sleep is assumed after a predetermined period of time and the occurrence of one movement. Thus the detection of the sleep posture or the alerting of the person is activated only after a predetermined period of time, e.g. 20 minutes, and starts with the alerting of the person after the person has made a first relevant movement, e.g. a first turn. Hence, for example, a person is allowed to fall asleep in a certain body posture, e.g. on his back. If the person after the exemplary 20 minutes is still on his back there will still be given no alarm, although this is a posture in the range in which an alarm should be given. Only after the person has turned one time and, after that, turns on his back again, there will be given an alarm.

In a further alternative the state of sleep is detected and the alerting of the person is activated at the occurrence of specific movement. Thus the detection of the sleep posture is activated only after sleep is detected, and after the person has made a first relevant movement, e.g. a first turn, the alerting of the person is activated. Hence, for example, a person is allowed to fall asleep in a certain body posture, e.g. on his back. If the person is detected to be asleep and is still on his back there will still be given no alarm, although this is a posture in the range in which an alarm should be given. Only after the person has turned one time and, after that, turns on his back again, there will be given an alarm.

In all four above mentioned approaches the user is allowed to fall asleep in the posture he/she finds most comfortable.

With the known method and apparatus according to U.S. Pat. No. 6,057,767 feedback (alarm) may be given to the user during an undefined period of sleep, which may cause a user to wake up during the night. When providing feedback in lighter sleep stages, people can generally react to these as the reaction threshold is low. In deeper sleep stages however, the reaction threshold is high. Providing feedback during the deeper sleep suggests that a user needs to be awakened, or brought to lighter sleep stages in order to react to the provided feedback. The result is that through these repeated awakenings, the natural sleep is disturbed.

According to another aspect of the present invention a sleep stage of the person is detected, wherein—when it is detected that the person is in a lighter sleep stage—the detection of the sleep posture or the alerting of the person is activated such that, in the event that his/her body posture is out of the predefined body posture range, the person will be alerted. The person is preferably only alerted when he/she is in, or shifts into a lighter sleep stage. This lighter sleep stage is preferably determined by the amount of body movement made by the user. Preferably, this body movement is of such magnitude, that it results in a change in the sleeping posture. Preferably, the movement should be detected for at least three seconds to determine that it is a lighter sleep stage or micro arousal. As an alternative or in addition, the sleep stage may also be determined by measuring the brain activity of the person.

According to this aspect of the invention the feedback (alarm) is given on moments most optimal for the user and disturbing the natural sleep as little as possible. Preferably, these moments are chosen when users are most able to react to feedback, which is in general in the lighter sleep stages or when awake (caused by natural internal processes of the user). When a user is provided with feedback when the user is in a lighter sleep stage or whilst being awake, it is easiest for a user to respond to this feedback. By the timing of the feedback therefore, the effectiveness of the sleep posture correction method is increased (it is easier for a user to respond) and the comfort level is remained as high as possible. This is because the natural sleep pattern is disturbed as little as possible.

General literature in the field of sleep describes lighter sleep stages as the lightest two stages (S1 and S2 or N1 and N2) of the four non-rem sleep stages recognised (S1 to S4 or N1 to N4). Alerting of a person can also be timed during moments of full wakeness (W) or moments of rem sleep (REM or rapid eye movement).

Alerting of a person is intended to be timed during arousals or micro-arousals occurring during sleep. In literature, a (micro) arousal is described as a short moment of wakeness or lighter stage sleep. It can be caused by various internal processes or stimuli or by various external stimuli. In literature, an arousal is recognised as such when it takes longer than 3 seconds and micro-arousals last between 3 and 10 seconds.

Preferably, the lighter sleep stage is determined by detecting the amount of body movement of the person. More preferably, this state of light sleep or being awake is determined by body movement that has a durance of longer than a predetermined period of time, preferably 3 seconds. It was found that after 3 seconds people can enter awakening or an (micro) arousal—a short period of light sleep or awakening that occurs naturally and frequently in sleep, in which people have an increased awareness of the outside world. By waiting for this period in an event of body movement (which results in a change of body posture), the chance to provide feedback during a moment of lighter sleep or an (micro) arousal event is increased.

Preferably the feedback (alarm) is adapted to the reaction threshold level of the user, taking into account the sleep stage the user is in. By adjusting the alarm or stimulation signal to the threshold level that the user is in, the proposed invention is effective because the stimulation is never too low to remain unnoticed by the user. On the other hand the adjustment to the threshold level provides comfort to the user, because the stimulation is never too high to become irritating and uncomfortable. Thus the solution effectiveness and the comfort level are increased.

According to yet another aspect of the invention a non-continuous feedback is provided, such that it is prevented that natural behavior and physiology cause a user to get used to the feedback, and such that it causes a user to feel the urge to respond. Thereby the solution effectiveness is increased as the users do respond to the proposed invention. Thus effective feedback is provided thereby avoiding unnecessary lengthly feedback and maintaining a high comfort level.

Preferably, this non-continuous feedback is provided by a non-continuous pattern. Preferably caused by sensory stimuli (preferably vibrotactile). Preferably the non-continuity in the feedback is provided by for example a feedback signal variation in frequency, duration, intensity and/or other parameters. The proposed invention will preferably be using signal variation through a varying signal frequency and intensity.

In particular it is envisaged that the alarm given by the alarming device—when it gives an alarm—is pulsating with an alarm frequency and/or alarm amplitude that increases in time.

According to yet another aspect of the invention an alarm is only given for a predetermined maximum time period, e.g. 10 to 60 seconds. This aspect of the invention provides the possibility to the user to not respond to the alarm generated without it causing discomfort, e.g. disturbance of sleep, discomfort to the body and/or other factors. In a further elaboration of this aspect the alarm is deactivated after the predetermined maximum time period until the next posture change is made. Preferably, this period before deactivation starts before a user falls back into their deeper sleep after an (micro) arousal.

According to yet another aspect of the invention, the alarm is given only in a part of the occasions where a sleep posture out of the predetermined body posture range is detected. Preferably, the number of given alarms is initially 30% of the times the person turns into a wrong position at the start of use, and increasing to 100% of the time after a certain period of time. Preferably this period of time is one to two weeks.

Because the learning process may take a while and it might be hard for users to (comfortably) sleep in the new positions immediately, this aspect of the invention takes into account the learning period of users in learning to sleep in new positions. By not fully applying the correctional activation stimulation from the beginning, users are provided with time and space to learn to sleep in their new positions. By taking this learning period into account, the comfort level of the proposed invention is maintained. Through the high comfort level and respect for the natural learning behaviour, it is likely for users to find it easy to continue using the proposed invention. Continued use enhances the learning process of sleeping in a new posture and that way the final solution effectiveness is increased.

The reaction of the person on a given alert may be detected, e.g. by a sensor, which preferably is the body posture detecting sensor. Thereby the reaction level of the person may be determined, e.g. after what period of time or at what frequency or amplitude does a user react to an alert signal? The number of given alerts to the person may be increased from a lower limit of the times the sleep posture is out of a predetermined body posture range at the start of use, and increasing to an upper limit of the times based on the determined reaction level of the person.

In still another aspect of the invention, the control unit of the apparatus is programmed to be set into a storage and diagnosis mode in which measurements from the body movement detecting sensors and/or sound detecting sensors of the apparatus are stored and diagnosed to analyse the user's sleep. The feedback activation is switched off during this period of time. Preferably, the proposed invention diagnoses the user's sleep (and possible illnesses or disturbances) through a combination of parameters. Preferably, these parameters are sound, position and movement, for example, combining sound measurements with body posture measurement to determine positional snorers, or for example combining breathing disturbances as seen in apnoea with body posture measurement to determine positional apnea. Preferably, the apparatus analyses the measured parameters and suggests the right therapy for a patient, e.g. positional therapy for a positional apnoea patient, positional therapy for a back snorer, positional therapy for a stomach sleeper, or others.

It should be noted that the above mentioned aspects of the invention can be applied in a method or apparatus either separately or in combination with any one of the other above mentioned aspects of the invention.

For example in a possible method and apparatus performing said method, the detection of the sleep posture or at least the alerting of the person, when his/her body posture is out of the predefined body posture range, is activated when a certain level of sound is detected and when thereafter increased body activity is detected. Increased body activity may be detected by detecting a turning movement of the person, and/or an increased movement during time of the person, and/or certain brain activity of the person and/or a certain heart beat of the person and/or a certain respiration of the person.

In another example the detection of the sleep posture or at least the alerting of the person, when his/her body posture is out of the predefined body posture range, is activated after a predetermined period of time and when after said period of time has lapsed increased body activity is detected.

In yet another example the detection of the sleep posture or at least the alerting of the person, when his/her body posture is out of the predefined body posture range, is activated after a predetermined period of time and when after said period of time a lighter sleep stage is detected.

Also other examples of combinations of the above described aspects of the inventions are conceivable and hence the above three examples may not be regarded as limiting.

The methods and apparatus according to the proposed invention can be used for positional therapy or for other applications in which a (body) posture is to be diagnosed, defined, measured, communicated, analysed and/or corrected (standalone or in combination with other parameters). Fields of application therefore are situations in which it is desired to monitor different aspects of the (body) posture, e.g. angle, position, duration, movements, activity, and more, or other elements that can be determined by (body) posture, movement and/or acceleration, e.g. wakeness/alertness, heartbeat, and more. For example to provide information and/or prevent problems and/or solve problems which can be determined by posture, e.g. neck- and back problems, snoring, sleep apnoea, bed sores, sudden infant death syndrome, and more. Another example is to provide information and/or prevent problems and/or solve problems which are movement dependent/can be determined by movement, e.g. sleep state, sleep in general, general sleeping problems, insomnia, restless leg syndrome, and more. The proposed invention could also be used for example to provide information and/or prevent problems and/or solve problems which are activity dependent/can be determined by activity, e.g. actigraphy, sleep disorders, sleepwalking, and more.

The invention will be elucidated in the following description with reference to the drawings.

DETAILED DESCRIPTION

Figure 3:
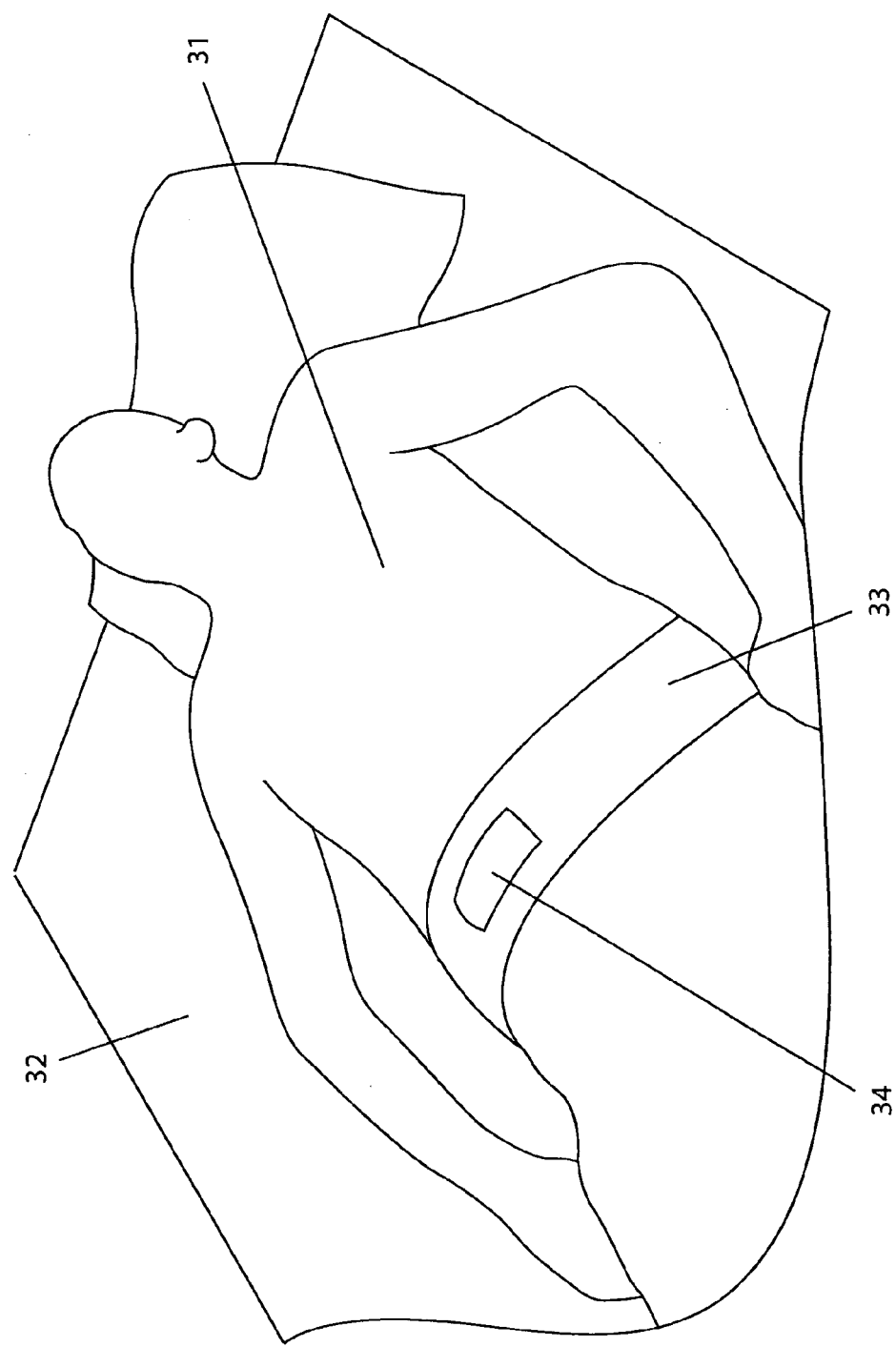
FIG. 3 shows schematically a lying person wearing an apparatus according to the invention on his body by means of a strap.
Figure 4:
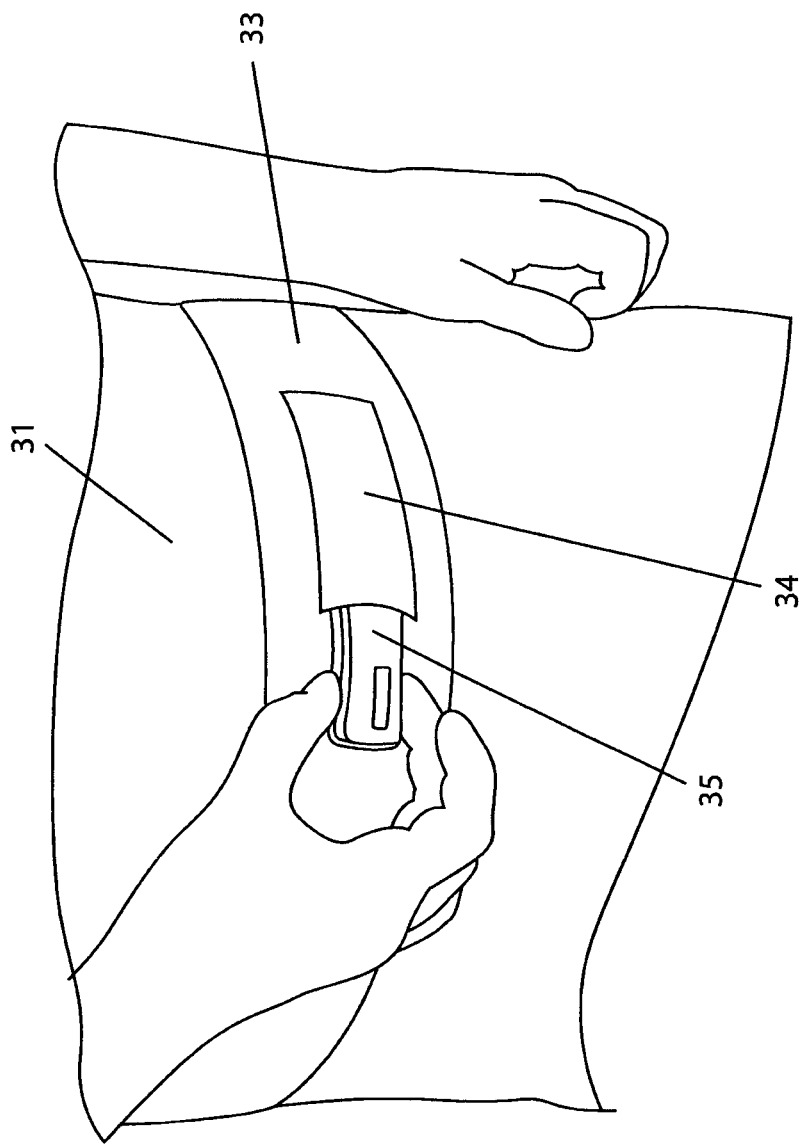
FIG. 4 illustrates how the apparatus is arranged on the strap of FIG. 3.

In FIG. 3 is shown a person 31 lying on a bed 32. The person 31 is wearing a strap 33 around his waist. The strap may also be worn around the chest or other position on the torso. In the middle of the strap 33 a pocket 34 is arranged in which a sleep posture alerting apparatus 35 is received as can be seen in FIG. 4.

Instead of a strap the apparatus 35 may also be worn in a dedicated pocket in a tight shirt. It is also possible to use a clip to attach the apparatus to a strap, belt or underwear, possbly underwear in which the device can be put. Other means like buttons, Velcro or other attaching methods could be used to place the device on nightwear. Also rings that use fabric (of for example a t-shirt) to hold the invention in place could be possible. Also other means for attaching the apparatus 35 to the body are conceivable. Essential is only that the apparatus is attached to the users body, in particular to the torso, so that the movements and orientation of the body of the user 31 are correctly related to the movements and orientation of the apparatus 35.

Figure 1:
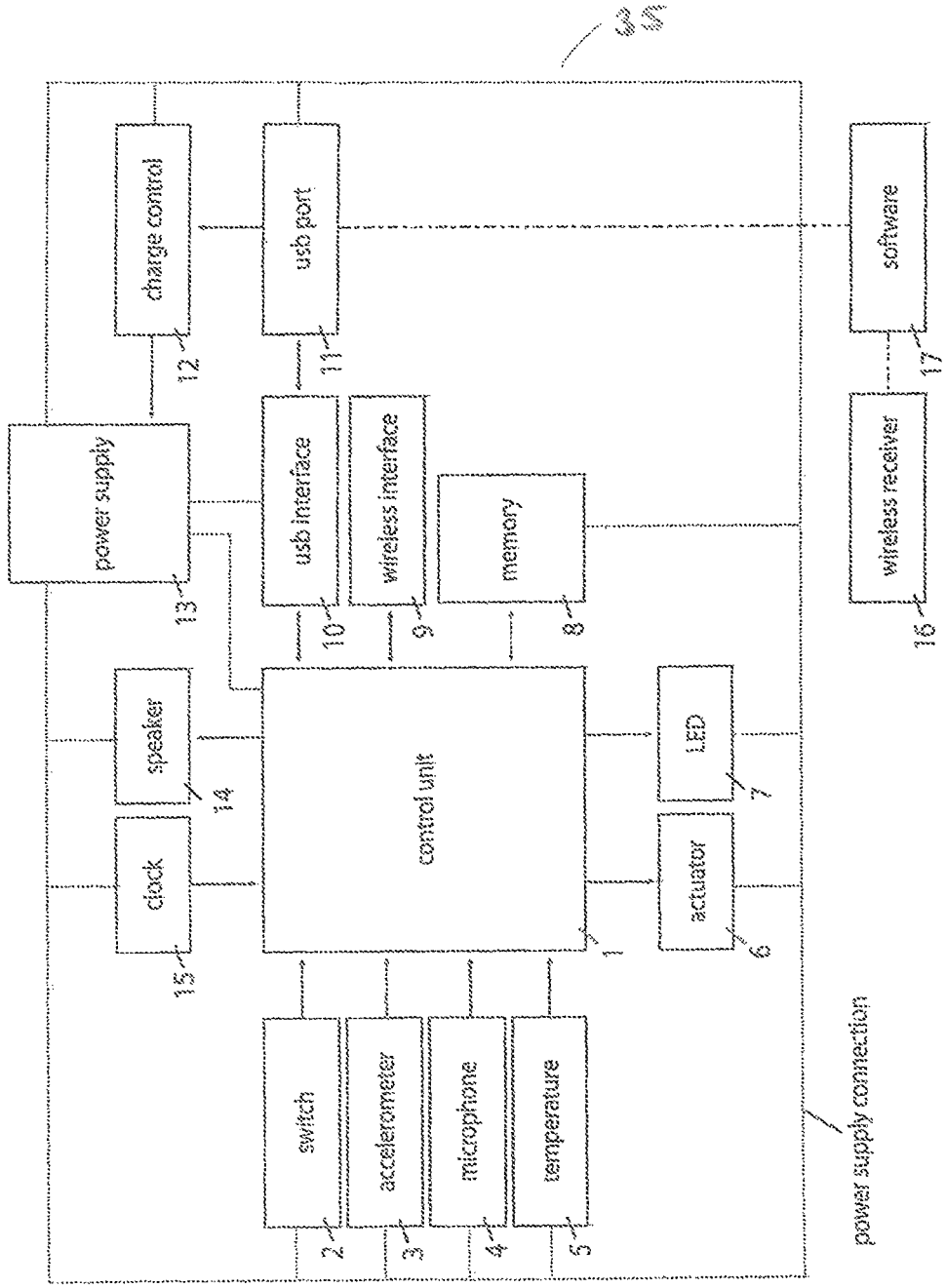
FIG. 1 shows diagramatic representation of a preferred embodiment of the apparatus according to the invention.

FIG. 1 is an illustration of a possible component structure of the apparatus 35. The components are all directly or indirectly connected to control unit 1. The control unit 1 enables the communication between the different components and the interpretation of the signals in between the components. The communication and interpretation of the signals is defined through a method, or so-called algorithm, of the control unit 1.

The control unit is in particular a programmable microcontroller which enables the communication between and the control of the hardware components. The control unit makes it possible to transfer all the signals between the different hardware components and external applications/products connected to the device. Furthermore it enables the programming of the behaviour of the apparatus and so to tell it how to respond to situations (e.g. accelerometer values, feedback, snoring sound, upright posture, and more).

The apparatus 35 furthermore includes a gravity actuated sensor 3 (cf. FIG. 1). Preferably the gravity actuated sensor is an electronic three-axes accelerometer/3-axes MEMS accelerometer to define the posture of the apparatus in three dimensions which is directly related to the posture of the body of the user 31. The introduction of a MEMS accelerometer is preferred because of the high frequency of measurements and fast response time to small changes in acceleration.

The apparatus also includes an alert device. In principle any type of alert that is noticed by the user in the specific circumstance, e.g. smell, sound, sight, taste and tactile—electronic stimulation, vibrotactile, or any other may be applied. Preferably however the alert device is adapted for vibrotactile stimulation of the person 31, preferably by a vibration motor 6. The use of vibrotactile feedback is preferred because it is comfortable in that it does not hurt or injure the user 31 (like with electronics shocks) and does not disturb the sleep rhythm of fie user 31 or partner of the user 31, like e.g. with sound.

Additionally the alert device may include a speaker 14 for audible feedback to the user 31.

The alert device may additionally be provided with a connection to other devices to enable remote monitoring by another individual, for example caretakers, nurses, parents or other family members.

The apparatus 35 may include a display, preferably a LED display 7 to give visual feedback to the user. The introduction of a LED will enable the apparatus 35 to transfer information using visual feedback to the user 31 to indicate e.g. battery status, stored events, operation mode, progress, occupation, and more.

The apparatus 35 may have a sound sensor, preferably a microphone 4 to detect noise or sound level from the environment, possibly to detect snoring, possibly to register disturbances. The introduction of a sound sensor enables the detection of snoring sounds so that even if the user is snoring in the desired position a type of feedback is activated b change position or posture (e.g. so that the partner does not have to do so) and therefore the device is optimised to prevent snoring.

The apparatus may be provided with a data storage device, preferably a memory 8 to store detected and measured events. Registering events makes it possible to gather information about what is going on at a certain moment during the sleep. This can be used at another moment in time to determine, inform, diagnose, help and/or advise users or others of various elements. This may be feedback to the user, information about sleeping/sleep monitoring, combine the storage of events with a certain action to indicate something to the user, make calculations, averages, figures, etcetera.

The apparatus may be provided with a feature to transfer stored data, preferably a USB interface 10 to enable connecting the apparatus 35 to a personal computer. The ability to transfer stored data enables a lot of options to combine the apparatus 35 with other appliances/software/products to enhance the capabilities of the stored events. This way information can be transferred or exchanged between appliances/products/software to offer new features to the user or give them more insight in the information stored in the apparatus 35.

The apparatus 35 may have external communication through a USB interface 10, but alternatively or additionally through a wireless interface 9 for communication with a computer or other devices. The communication with external devices, e.g. a personal computer, babyphone, or other, enables the exchange of information between those devices and enables options for information feedback, remote monitoring or remote control.

The apparatus 35 has a power supply 13, preferably an integrated battery to enable wireless use of the apparatus 35. The integration of the battery makes it possible to use the apparatus 35 wherever wanted without the need of a wall plug. Furthermore it makes the apparatus 35 wireless, which improves the comfort for the user 31 and the freedom to move in/around/away from the bed or sleeping area.

The apparatus may have a charging system 11, 12, preferably including a USB port 11 which enables charging the battery of the apparatus 35 through an adapter or a personal computer. Charging the battery with a charging system 11, 12 means the user does not have to open up the apparatus 35 and/or to change the batteries to keep using the product. This minimises the occurrence of problems to the apparatus 35 and makes it easier to supply it with required power. Preferably a charging system based on induction or exchange of movement to enable the charging of the battery without the need for an opening in the housing, such that the apparatus can be made moisture/waterproof.

The apparatus 35 may include a temperature switch, preferably an integrated circuit temperature switch to define overheating of electronic components to disconnect power supply if temperature exceeds a certain threshold value. Thus, to prevent overheating of the, device and minimise the risk.

The apparatus may include a temperature detection means, preferably an integrated temperature sensor 5, additionally an external temperature sensor connected to the device to detect for example body temperature to define sleep comfort, which may be especially important for monitoring babies. The introduction of an integrated temperature sensor 5 enables measurement of the temperature of the body to enable more options of feedback and sleep information. First of all the user can be indicated of a high temperature during sleep to improve the quality and comfort of the sleep. Also it is possible to alarm in certain situations and information can be given to the user about the body temperature during sleep; especially with babies or children. For babies, correct temperature of the body during sleep is very important.

Furthermore the apparatus 35 may be provided with additional integrated detection means (not shown), like e.g. a sound sensor, shock sensor, humidity sensor and more for additional functions like detection of respiration, snoring sound, environmental influence factors and more. Moreover the apparatus 35 may have connectors (not shown) for external sensors; e.g. position sensors, shock sensors, respiration sensors and more for additional functions like detection of respiration, breathing pattern, heart rate, muscle movement, snoring, apnea and more.

The apparatus 35 includes an internal clock 15, preferably crystal oscillator to provide the time and data to the control unit. The internal clock 15 enables the registration of events in relation with time to create a timestamp for the event. In this way the time the event took place can be defined more precise for storage into the memory 8 and/or feedback (alert) through information given to the user 31.

The apparatus may be supplied with software which can be loaded on a computer. The software program may be used to download, store, analyse, display, visualise and/or transfer data from the apparatus to the computer 35. The software program enables the interpretation, visualisation and comparison of the events and data stored by the apparatus to enable feedback of events. This way events registered at a certain moment can be communicated at another moment in time through which the user 31 can be informed about their behaviour. The most beneficial result of this is that it is possible to guide and train the user 31 into sleeping with an improved sleeping posture by giving more insight and to stimulate the use of the apparatus 35. Preferably the software can be used to combine parameters, values, functions, and more between the proposed invention and external products or appliances that can be connected to the personal computer or through the world wide web.

The apparatus 35 has a switch 2 which is connected to the control unit 1 to activate it. Whenever the apparatus 35 is activated, the accelerometer 3, microphone 4 and temperature sensory means 5 execute measurements to be transferred to the control unit 1 for interpretation.

The accelerometer 3 returns values for the accelerations measured in all three dimensions x, y and z. From these values the activity, movement and or position can be derived. The microphone 4 returns values for the frequency and amplitude of the measured sound. The temperature sensory means 5 returns values for the temperature measured in its environment (e.g. body temperature, device temperature and more).

Whenever the signals from the accelerometer 3, microphone 4 or temperature sensory means 5 exceed a predefined threshold, e.g. undesired body posture or snoring, when interpreted by the control unit 1 the actuator 6 (i.e. the vibration motor) is activated to indicate the user 31 that the body position needs to be changed.

Whenever visual feedback to the user is needed the control unit 1 activates the LED display 7 to switch on the light of the LED display 7 in a predefined sequence.

Whenever an event takes place within the control unit 1 which is predefined to be stored it is done so by sending a signal from the control unit 1 to the internal memory 8. The control unit 1 can also retrieve information stored into the memory 8 whenever necessary.

Whenever a wireless interface 9 is connected to the control unit 1 the apparatus 35 is able to communicate through the wireless interface 9 with a wireless receiver 16 of an external device.

Whenever an external device is connected to the device through the USB port 11 signals are exchanged between the USB port 11 and the control unit 1 through the USB interface 10. The USB interface 10 translates the signals from the USB port 11 into signals to the control unit 1 and vice versa.

Whenever an external device is connected to the device through the USB port 11 power can be transferred to the power supply 13 with the use of a charge control 12. The charge control 12 enables the transfer of electronic power from the USB port 11 to the power supply 13.

The power supply 13 is connected to all components within the device which have to be supplied with electronic power. The electronic power transferred from the power supply 13 to the control unit 1 is measured by the control unit 1 to define the status of the power supply 13.

Whenever a speaker 14 is connected to the control unit 1 it is possible to sound an alarm or produce sound through the speaker 14.

The clock 15 is directly connected to the control unit 1 to provide the control unit 1 with the values to define the date and the time. This information from the clock 15 is used to store the date and time for events stored from the control unit 1 into the memory 8.

Whenever communication through the USB port 11 or wireless interface 9 is possible with software from an external device 17 the control unit 1 can exchange information or programs with the software 17.

Figure 2:
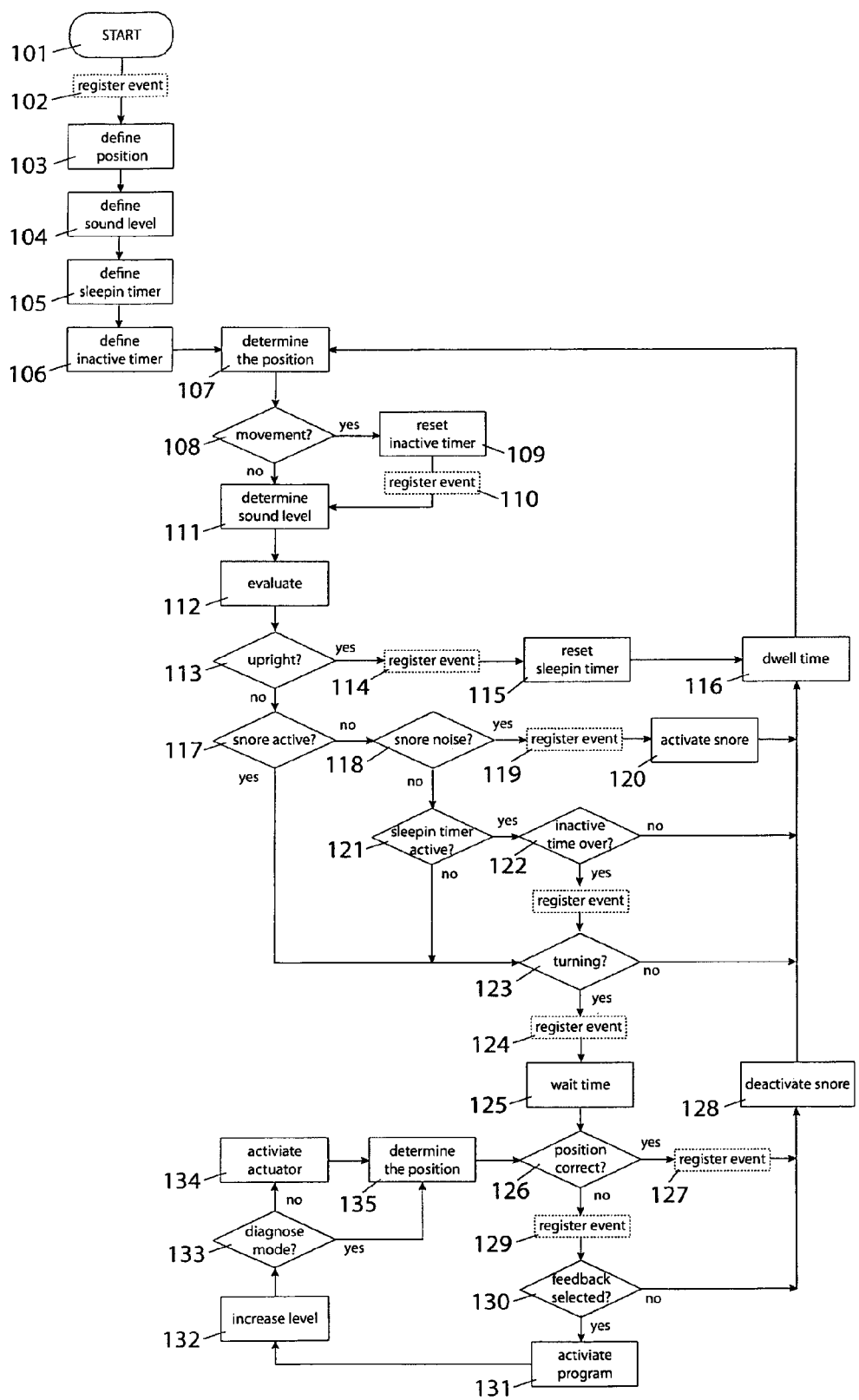
FIG. 2 shows a flow chart representing a procedure for automatic correction of sleep posture according to the invention.

FIG. 2 is a flowchart which illustrates the procedure of a method for correcting the sleep posture of a person using the apparatus of FIG. 1.

After starting up the apparatus in step 101, which is registered into the memory at step 102, the position of the user is firstly determined in step 03 and the sound level of the environment in step 104. Then the timers for the sleep-in timer and inactive timer are defined and activated respectively at step 105 and step 106. These timers are defined to be countdown timers which start at a typical value and countdown to zero at which it is defined as inactive. The output signals of the sensors are evaluated in step 7 with respect to a position, in particular a rotational position about a longitudinal axis of the body (acceleration in x, y or z).

At step 108 it is determined whether movement is present to control the inactive timer. If movement is detected at step 108 the inactive timer is reset to the countdown value at step 109 and the event is registered at step 110. If no movement is detected at step 108 the program continues with step 111. The registration at step 111 determines at step 112 whether or not the determined posture is in the upright position which indicates that the user is awake. If it is determined in step 113 that the position is upright then this upright position is registered at step 14 and the sleep-in timer will have to be reset at step 115 to start counting down again. After that a predetermined time, a so-called dwell time at step 116, is waited for, until the processing returns to step 107.

Subsequently, the steps 107 to 113 will rerun. If it is determined at step 113 that the position it not upright it is indicated that the user is lying down in order to sleep. While the user is in the lying position and falling asleep it is determined at step 117 whether snoring was detected in a previous run of the program. If no snoring was detected in a previous run of the program the program detects at step 118 whether the user is snoring or not at that time. If it is detected at step 118 that the user is snoring this is registered and stored at step 119 and the snore counter is activated at step 120 to indicate the presence of snoring for the next round. After the snore counter is activated at step 120 the program continues to the dwell time at step 116. After that a predetermined time, a so-called dwell time at step 116, is waited for, after which the processing returns to step 107.

If it is determined in step 118 that the sound level determined at step 111 cannot be indicated as snoring it is determined at step 121 whether the sleep-in timer is active, or in other words finished counting down to zero. If it is determined at step 117 that the sleep-in timer is active, and thus the user should not be indicated about the body position, the inactivity timer is consulted at step 122. If the inactive timer is still active, thus indicating that the user is not in sleep state, a predetermined time, a so-called dwell time at step 115, is waited for, until the processing returns to step 107. If it is determined at step 122 that the user is in a sleep state, thus indicating that the user has not been active for the period of the inactive timer, the event is registered at step 119 and the program continues to step 120. If it is determined at step 121 that the sleep-in timer is not active it is determined at step 123 whether body movement activity is present.

If it is detected at step 117 that the snore counter is active, and thus snoring was detected in a previous run of the program, the program continues to step 123 immediately to determine whether body movement activity is present.

If it is determined at step 123 that no body movement is present a predetermined time, a so-called dwell time at step 116, is waited for, until the processing returns to step 107. If it is determined at step 123 that body movement is present the event is registered at step 124 and the wait time is activated at step 125. For a predetermined time, a so-called wait time, is waited for, until the processing continues to step 126 to determine whether the body posture is correct.

If it is determined at step 126 that the body position is correct a predetermined time, the snore counter is deactivated at step 128 and to a so-called dwell time at step 116, is waited for, until the processing returns to step 107. If it is determined at step 126 that the body position is incorrect the event is registered at step 129 and it is defined at step 130 whether the actuator program is to activated at step 131. Step 130 is programmed to respond to a training program function in which it is defined whether the feedback should be activated or not due to limited feedback in the period of the first weeks of use. If at step 130 it is defined that feedback is to be executed the program is activated at step 131.

Subsequently the level of the actuator program is increased at step 132 and the program continues to step 133. At step 133 it is defined whether the diagnose mode of the proposed invention is active, in which all events should be stored but no feedback should be given to the user. When it is defined at step 133 that the diagnose mode is inactive the program continues to step 134 to activate the actuator, thus give feedback to the user, and continue to step 135 in which the position is defined from the values for acceleration. When it is defined at step 133 that the diagnose mode is active the program will skip step 134, thus no feedback is given to the user, and continue to step 135 in which the position is defined. From step 135 the program continues to step 126 in which it is defined again if the position of the user is correct.

Some of the steps mentioned in the above will be described in more detail in the following:

Determining the Position (Step 107)

The position of the user is defined by the proposed invention through the values for acceleration in the x, y and z direction. The algorithm is repeated in a fast pace (preferably 10 Hz) and so the program is run 10 times per second to determine the position/posture of the user.

Dwell Time (Step 116)—Parameter Definition Frequency/Program Cycle Time

The dwell time is introduced to control the number of measurements over a given period of time. The minimum amount of measurements is preferred to be at least once per second. The dwell time for the proposed invention is programmed somewhere between 1 and 100 Hz preferably at 10 Hz. Thus, the time between two cycles of the program is one-tenth of a second.

Movement (Step 108)—Activity

The movement of the user is defined by accelerations in x, y or z direction which exceed a preset threshold value for indication of movement.

Inactive Timer (Step 106/Step 109)—Sleep State

The inactive timer is introduced to define the sleep state of the user from a predefined period of inactivity, thus the absence of movement. The timer is a timer which starts counting down (towards zero) or count (towards a certain threshold value) to evaluate the absence of movement for a preset period of time. When the count(down) timer exceeds it threshold value it is indicated that the user is in state of sleep and a change of posture (step 126) will result in feedback to the user, possibly even within the sleep-in time period, which is preferably 20 minutes.

Determining Sound Level (Step 111)—Sleep State

The sound level is defined to detect the presence of snoring sound to be used in steps 117 and 118.

Upright Position (Step 113)—Sleep Position

Whenever an upright position is detected by a threshold value on the axis related to the spine of the user the sleep-in timer is to be reset. Whenever the position is upright the period of sleep-in timer countdown is not activated.

Sleep-in Timer (Step 105/Step 115/Step 121)—Undisturbed Sleep-in Period The sleep-in timer is introduced to make sure the user of the proposed invention is able to fall asleep in each preferred position, thus as well the undesired position to which the proposed invention is predefined to activate the actuator. For the period in which the sleep-in timer is counting down from the predefined time the actuator will not be activated through the detection of an undesired position. The average sleep-in period for a proposed invention is programmed somewhere between 0 and 120 minutes, preferably between 10 and 30 minutes. The sleep-in timer can be interrupted by the detection of snoring (step 117/step 118) or inactivity, thus sleep state (step 122) so the proposed apparatus can activate the feedback within the sleep-in timer period.

Snore Active (Step 117/Step 118/Step 120)—Sleep State

Whenever snore is detected within the sleep-in timer, and thus the user is in a state of sleep, the sleep-in period should be ignored and the proposed invention should be able to respond with feedback to an undesired posture. Whenever snore sound is detected at step 118 (determined at step 111) the snore counter is switched on/activated. This means that in the next cycle of the program the program will not continue to step 118 after being defined at step 117 and thus, within the sleep-in timer period, the activity is defined at step 123 and the proposed invention will respond to a change in posture. The snore counter can than only be deactivated after the posture is changed (step 128) and thus the presence of snoring sound is defined again in the next loop.

Wait Time (Step 125)—State of Arousal

The wait time is introduced to make sure the user is in a state of arousal and thus in which the user can respond consciously to the actuator. Whenever body movements exceed a threshold value (step 123) and still exist after a period of 3 seconds it can be stated that a state of arousal is present. Therefore the actuator is activated only after three seconds from the moment body activity is measured through the accelerometer. The minimum period of time to wait is 3 seconds, preferably 3 seconds since then the actuator is activated at the start of the arousal. A wait time is therefore introduced at step 125.

Feedback Selected (Step 130)—Learning Curve

With the standard programming of the proposed invention the sensor will respond with feedback each time an undesired posture is detected. It might be possible that users will have to get used to the feedback signal and therefore wake up because of it. Therefore, when the user starts using the sensor for the first time it can be programmed not to respond to every undesired posture and increase the response over time. The decreased program should increase between 0% and 100% over a defined period of time, preferably from 30% to 100% over a period of 7 to 14 days. To introduce this into the algorithm step 130 is introduced to make it possible to include or exclude the feedback program upon a detection of an undesired posture. The implementation of the learning curve could be conceived as follows (1=feedback upon undesired posture; 0=no feedback upon undesired posture).

33%=1-0-0-1-0-0-1-0-0-1-0-0-1-0-0-1
50%=1-0-1-0-1-0-1-0-1-0-1-0-1-0-1-0
66%=1-1-0-1-1-0-1-1-0-1-1-0-1-1-0-1
100%=1-1-1-1-1-1-1-1-1-1-1-1-1-1-1-1

Activate Program (Step 131)—Feedback Pattern

The activate program is introduced to both lower the risk of awakening the user and to lower the risk of habituation by the user to the actuator signal. In order to lower the risk of awakening the user it is important to start the actuator program with a lower strength and lower frequency signal and increase over time up to the user specific threshold to respond to the actuator. In order to lower the risk of habituation it is important that the actuator program varies over time and thus the actuator signal is not the same as the previous actuator signal. By the incremental strength and frequency of the signal due to the risk of awakening the user also the risk of habituation by the user is lowered. The activate program is activated and maintained during the arousal. The average period of time for an arousal is between 15 and 30 seconds. The activate program is run for a maximum period of 1 minute, preferably 30 seconds.

Diagnose Mode (Step 133)—No Feedback and Registration of Events

For monitoring, feedback, diagnosis purposes and other appliances the events from the proposed invention are stored into the memory. While the proposed invention is activated it can register the values measured by all detection means, position of the body, activation of the feedback signal, and more. The proposed invention is able to store all events that are measured or initiated by the proposed invention. To optimise the memory of the sensor it can be chosen to store only specific registered events. Preferably during diagnoses the user is not awakened and thus the feedback program is switched off (step 133) so the proposed invention does register all events but no feedback is given to the user.

Software—Feedback and Combination with Other Appliances

The registration of events is performed by storage into the memory of the proposed invention. Through the use of software this information could be communicated to a personal computer, the world wide web or other appliances connected to the proposed invention. The communication between the apparatus and external devices is not included in the algorithm but is an active element within the apparatus to be included for multiple purposes.

Programmable—Reprogram Proposed Invention

The software programming is introduced to give the user the advantage of changing the behaviour of the controller 1 of the apparatus. This way the value of each parameter is reprogrammable and the control unit 1 can be reprogrammed to e.g. respond to different values for the angles detected by the accelerometer 3, respond with lower or higher strength to different values for the angles detected by the accelerometer 3 and/or respond less or more often to the angles detected by the accelerometer 3 and more. Certain steps within the algorithm should therefore be able to be switched on or off to define the behaviour of the sleep posture alerting apparatus.

The invention claimed is:

1. A sleep posture alerting apparatus, comprising:
an electronic control unit,
a body posture detecting sensor operatively connected to the control unit for detecting a posture of a person's body, and
an alarming device operatively connected to the control unit,
wherein the sleep posture alerting device has a normal operational mode, in which—when the posture of the body detected by the body posture detecting sensor exits a predefined posture range—the control unit sends an alarm signal to the alarm device, and the alarming device generates an alarm based on the signal received from the control unit, to alert said person, wherein the control unit is programmed to switch the sleep posture device in said normal operational mode after an initial sleep-in time period, in which the control unit comprises a sleep-in timer which is defined for setting the sleep-in time period, wherein said control unit is programmed to activate and reset the sleep-in time based on an evaluation of an output signal of the body posture detecting sensor which determines whether or not the detected posture of the body is in an upright position.

2. The apparatus according to claim 1, wherein the control unit is programmed to reset the sleep-in time period when the person gets up.

3. The apparatus according to claim 1, which comprises a sleep detecting sensor connected to the control unit adapted to detect whether the person is in a state of sleep.

4. The apparatus according to claim 3 further comprising at least one of:
the sleep detecting sensor is a body activity detecting sensor, a heartbeat sensor, a brain activity detecting sensor, and wherein the control unit is programmed to determine whether the person is asleep based on a level of body activity per time period detected by said sleep detecting sensor, wherein the sleep detecting sensor is a sound detecting sensor adapted to detecting respiration or snoring sounds and wherein the control unit is programmed to determine whether the person is asleep based on a sound level and/or frequency produced by the person and detected by said sound detecting sensor.

5. The apparatus according to claim 1, wherein the apparatus comprises a sleep stage detecting sensor connected to the control unit, and wherein the control unit is programmed to determine a specific sleep stage of the person based on a signal of the sleep stage detecting sensor, whereby, when the apparatus is in the normal operational mode, the control unit sends an alarm signal to the alarming device, only when it is determined that the sleep stage is a lighter sleep stage, wherein, the sleep stage detection sensor comprises a body activity detecting sensor from the group consisting of a body movement detecting sensor, a brain activity measuring sensor, a heartbeat detecting sensor and a respiratory detecting sensor.

6. The apparatus according to claim 5, wherein the sleep detecting sensor is a body activity sensor a heartbeat detecting sensor, a brain activity detecting sensor, and wherein the control unit is programmed to determine whether the person is asleep based on the level of body activity per time period, and wherein the body activity detecting sensor for sleep stage detection and the body activity detecting sensor for determining the sleep state are one and the same sensor.

7. The apparatus according to claim claim 1 wherein the control unit is programmed to deactivate the normal operational mode when a person gets up.

8. The apparatus according to claim 1, further comprising at least one of the following features:
the control unit is programmed to send an alarm signal to the alarming device only in a predetermined part of the occasions where a sleep posture out of the predetermined body posture range is detected;
the control unit is programmed to increase the number of sent alarm signals from a lower limit of the times the sleep posture is out of a predetermined body posture range at the start of use, and increasing to an upper limit of the times after a certain period of time;
the apparatus has a sensor connected to the control unit to detect reaction of the person on a given alert, and wherein the control unit is programmed to determine a reaction level of the person and is programmed to increase the number of sent alarm signals from a lower limit of the times the sleep posture is out of a predetermined body posture range at the start of use, and increasing to an upper limit of the times based on the determined reaction level of the person;
the alarming device is a vibrator for providing a vibrotactile stimulation alarm to the person;
the control unit is programmed to provide an alarm signal to the alarming device which corresponds to an alarm frequency and/or alarm amplitude that increases during a predetermined period of time and/or use;

the control unit is programmed to provide an alarm signal to the alarming device which corresponds to a non-continuous alarm pattern frequency and/or alarm amplitude over time and/or use; and the control unit is programmed to provide an alarm signal to the alarming device only for a predetermined maximum time period.

9. The apparatus according to claim 1, wherein the body posture detecting sensor is a gravity activated sensor.

10. The apparatus according to claim 1, wherein the control unit is programmed to be switched from the normal operational mode into a storage and diagnosis mode in which measurements from the sensor of the apparatus are stored and diagnosed to analyse the user's sleep.

11. A sleep posture alerting method executed by a control unit, wherein a sleep posture of a person is detected by a body posture detecting sensor and wherein the person is automatically alerted by an alerting device when the sleep posture is out of a predetermined body posture range, wherein the alerting of the person, when his/her body posture is out of the predefined body posture range, is deactivated during a sleep-in time period, the method comprising the following steps:
  determining a position of a user by the body posture detecting sensor;
  defining a timer for a sleep-in timer setting the sleep-in time period;
  activating the sleep-in timer;
  evaluating an output signal of the body posture detecting sensor to determine whether or not the determined posture is in an upright position which indicates that the person is awake; and
  resetting the sleep-in timer in case that the determined posture is an upright position.

12. The method according to claim 11, wherein the timer is a countdown timer which starts at a typical value and countdown to zero at which it is defined as inactive.

13. The method according to claim 11, wherein a deactivated sleep-in period is reset when the person gets up.

14. The method according to any of the claim 11, wherein the alerting of the person, when his/her body posture is out of the predefined body posture range, is deactivated when the person gets up.

15. The method according to claim 11, wherein the alerting of the person is deactivated during an inactivity time period after a last detected movement, wherein the method comprises the following steps:
  defining a timer as an inactive timer to evaluate an absence of movement for a preset period of time;
  activating the inactive timer;
  evaluating an output signal of a body activity detecting sensor to determine a movement of the person; and
  resetting the inactive timer in case that a movement is detected.

16. The method according to claim 11 further comprising a step of ignoring the sleep-in timer by the detection of inactivity or snoring, so that the person is alerted within the sleep-in time period.

17. The method according to claim 11, wherein the state of sleep of the person is assumed after a predetermined period of time, after which the alerting of the person is activated such that, in the event that his/her body posture is out of the predefined body posture range, the person will be alerted.

18. The method according to claim 11, wherein the state of sleep of the person is detected and wherein when it is detected that the person is in a state of sleep, the detection of the sleep posture or the alerting of the person is activated such that, in the event that his/her body posture is out of the predefined body posture range, the person will be alerted.

19. The method according to claim 18, wherein the state of sleep is detected by detecting body activity of the person, wherein the body activity is selected from the group consisting of the amount of body movement, or through a detecting sensor measuring at least one of respiration, heartbeat, and brain activity.

20. The method according to claim 18, wherein the method further comprises the steps of:
  defining a state of sleep of the person from a predefined period of inactivity;
  starting the inactive timer to evaluate an absence of movement for a preset period of time; and
  alerting the person when the person is in an undesired posture in case that the inactive timer exceeds the preset period of time.

21. The method according to claim 18, wherein a sleep stage of the person is detected and wherein when it is detected that the person is in a lighter sleep stage, the detection of the sleep posture or the alerting of the person is activated such that, in the event that his/her body posture is out of the predefined body posture range, the person will be alerted.

22. The method according to claim 21, wherein the lighter sleep stage is determined by detecting the amount of body activity of the person.

23. The method according to claim 22, wherein the body activity is selected from the group consisting of the amount of body movement, brain activity, respiration and heartbeat.

24. A sleep posture correcting apparatus, comprising a control unit programmed to perform the method according to claim 11.

* * * * *

UNITED STATES PATENT AND TRADEMARK OFFICE
CERTIFICATE OF CORRECTION

PATENT NO. : 9,060,880 B2  
APPLICATION NO. : 13/695209  
DATED : June 23, 2015  
INVENTOR(S) : Eline Christiane Van Beest Page 1 of 1

It is certified that error appears in the above-identified patent and that said Letters Patent is hereby corrected as shown below:

On the Title Page:

After Item (76) Inventor, in column 1, line 2, Insert

Item --(73) Assignee Nightbalance B.V., Delft (NL)--.

Signed and Sealed this  
Second Day of August, 2016

Michelle K. Lee  
*Director of the United States Patent and Trademark Office*